United States Patent
Mayer et al.

(10) Patent No.: US 7,355,406 B2
(45) Date of Patent: Apr. 8, 2008

(54) METHOD AND MAGNETIC RESONANCE IMAGING APPARATUS FOR PLANNING AN EXAMINATION OF A SUBJECT

(75) Inventors: Klaus Mayer, Eckental (DE); Cecile Mohr, Erlangen (DE); Mike Müller, Möhrendorf (DE)

(73) Assignee: Siemens Aktiengesellschaft, Munich (DE)

( * ) Notice: Subject to any disclaimer, the term of this patent is extended or adjusted under 35 U.S.C. 154(b) by 82 days.

(21) Appl. No.: 11/482,456

(22) Filed: Jul. 7, 2006

(65) Prior Publication Data
US 2007/0161889 A1  Jul. 12, 2007

(30) Foreign Application Priority Data
Jul. 7, 2005  (DE) .................. 10 2005 031 901

(51) Int. Cl.
*G01V 3/00* (2006.01)
(52) U.S. Cl. ...................... 324/309; 324/318
(58) Field of Classification Search ........ 324/300–322; 600/407–455
See application file for complete search history.

(56) References Cited

U.S. PATENT DOCUMENTS

| | | | |
|---|---|---|---|
| 5,539,312 A * | 7/1996 | Fu et al. ..................... 324/309 |
| 6,195,409 B1 * | 2/2001 | Chang et al. .................. 378/20 |
| 6,363,163 B1 * | 3/2002 | Xu et al. ..................... 382/130 |
| 6,529,762 B1 * | 3/2003 | Ladebeck .................... 600/410 |
| 2002/0198447 A1 * | 12/2002 | Van Muiswinkel et al. . 600/410 |
| 2005/0154292 A1 | 7/2005 | Tank |

* cited by examiner

*Primary Examiner*—Brij Shrivastav
(74) *Attorney, Agent, or Firm*—Schiff Hardin LLP

(57) ABSTRACT

In a method for planning an examination of an examination subject in a magnetic resonance system, wherein images of different regions of the examination subject are acquired that are assembled into an overall image, the position of at least one first image in the examination subject, the measurement parameters for this at least one MR image are established, the position of at least one second image in the examination subject is determined, the measurement parameters for the at least one second image are established, and the measurement parameters that are dependent measurement parameters are determined. With these dependent measurement parameters the measurement parameters in the images are set (adjusted) such that they are identical for all images.

10 Claims, 3 Drawing Sheets

METHOD AND MAGNETIC RESONANCE IMAGING APPARATUS FOR PLANNING AN EXAMINATION OF A SUBJECT

BACKGROUND OF THE INVENTION

1. Field of the Invention

The present invention concerns a method for planning an examination of an examination subject in a magnetic resonance system, wherein images of different regions of the examination subject are acquired. The invention is particularly (but not exclusively) applied in magnetic resonance systems in which images of the examination subject are acquired at different table positions.

2. Description of the Prior Art

In magnetic resonance systems the trend has emerged toward ever-shorter magnet shapes in order to increase the comfort for the patient in the examination. In most examinations these shorter magnet shapes enable the head of the patient to not be enclosed by the magnet, so that the examination subject does not experience claustrophobic discomfort.

Such shorter magnets lead to the available field of view in the acquisition becoming ever smaller. In MR examinations the relevant image section of the examined body region likewise becomes ever smaller. It is simultaneously ever more difficult for the operator to cover (image) larger examination regions with only one examination.

Furthermore, MR techniques have been developed with which a larger region of the body can be examined, by shifting (displacing) the table on which the examined person rests through the magnets, so examinations are conducted at multiple table positions. Examination of regions of the body that are larger than the field of view available to the system are thereby possible.

According to the prior art, a body region that is larger than the available field of view is examined by data being acquired from a number of slabs or levels. The body region is thus deconstructed into individual segments, and a measurement protocol that can include a number of imaging sequences is implemented at an associated table position in each segment. For example, the entire body can be acquired by measurements at different body regions, this ensues at different slabs (table positions or imaging regions). The images that are acquired at each slab respectively have measurement parameters (such as, for example, echo time, repetition time, slice thickness, number of the slices, voxel size, slice orientation etc.) that are independent of one another. The problem now is that the operator has no possibility to establish a dependency between the individual slabs or the measurement protocol parameters. For example, if the operator changes the contrast at the third level of a whole-body examination, this contrast change is not automatically transferred to the measurements of the other slabs. When the individual images should be assembled into an overall image, however, specific parameters for all images must be the same so that, for example, images with various contrast ratios are not contained in the composite image. According to the prior art, in the case of parameter changes that should apply for entire multi-level examinations, the operator would previously have to adjust the individual parameter data sets manually for each level. The operator would consequently note each parameter change, open the measurement protocol for the next slab for processing and individually adjust each measurement parameter or each data post-processing step.

SUMMARY OF THE INVENTION

An object of the present invention is to simplify and to accelerate the planning of an examination of in a magnetic resonance system, of the type wherein the examination includes measurements (data acquisitions) at different table positions.

According to a preferred embodiment of the invention the invention comprises the following steps are executed. The position of at least one first image in the examination subject is determined first. The measurement parameters that are necessary for the acquisition of the MR image are likewise established. The position of at least one second image in the examination subject is furthermore established, and the measurement parameters for this at least one second image are likewise established. In a further step, the measurement parameters that are dependent measurement parameters are determined, which means that given these dependent measurement parameters being measurement parameters that can be set and then are set, (adjusted) to be identical for all images. This use of dependencies between the measurement parameters makes it possible to distinctly simplify and to accelerate the planning of an examination in a magnetic resonance system. This leads to a facilitation of work through a simple operation since the repetition of entire work steps, for example for changing a parameter for multiple slabs, is avoided. Furthermore, the generation of composite whole-body exposures or multi-slab overview exposures is significantly simplified.

In a preferred embodiment, given a change of a dependent measurement parameter in one of the images, this change of the dependent measurement parameter is transferred to the other images, while given a change of an independent measurement parameter (meaning of an individual parameter) this change of the parameter is not transferred to the other image. The change of measurement parameters in various measurements is thus simplified since the change of the measurement parameter effected at one imaging frequency is automatically transferred to the other imaging sequences.

The at least one first image and the at least one second image are advantageously acquired at different positions of the table on which the examination subject or the examined person is arranged.

Furthermore, a first measurement protocol with a first measurement protocol data set can be generated at a first table position and a second measurement protocol with a second measurement protocol data set can be generated at a second table position. The measurement protocol at the respective table position advantageously includes a number of imaging sequences for generation of the MR images at the various table positions. If a dependent parameter in one of the measurement protocol data sets is now changed, this change is automatically transferred to the other measurement protocol data sets.

Furthermore, it is possible that categories of dependent measurement parameters are determined, with a category encompassing those dependent measurement parameters whose values are the same for all images. A category describes a set of parameters whose values are the same for all measurement protocols that participate in an examination. Furthermore, the operator has the possibility to configure a category. This means that, from a pool of measurement parameters, geometric dependencies and data post-processing steps, the operator selects those between which dependencies should exist for a predetermined examination.

This newly-generated category can be stored under a predetermined name and is ready for a further application.

The categories preferably depend on the examined region of the examination subject. By selection of the examined region, the user can select the measurement parameters that should be the same for all measurements. For example, operating personnel can select the category "liver", which means that the measurement parameters that must be identical in this examination of the liver in order to obtain a meaningful image (that is assembled from the individual images) are identical. Furthermore, for example, it can be required that all acquired slices are situated parallel to one another. In another example, in the category "whole-body acquisition", it is necessary for the geometric parameters such as slice thickness, voxel size or slice interval to be the same for all measurements.

So that operating personnel can establish whether measurement parameters are dependent or individual, according to a preferred embodiment a dependent measurement parameter can be represented differently than an individual measurement parameter whose value is not the same for all images. For example, the dependent parameters can be represented with a cursive font while the other individual parameters are represented with a non-cursive font. Different color representations or an identification with different predetermined characters would also be conceivable.

In the planning of an examination, the operating personnel can now select a category that typically depends on the examination region. The dependent and the individual parameters are now established by selection of the category.

The invention likewise concerns a magnetic resonance examination system in which, as mentioned above, images of different regions of the examination subject are acquired, with these images being assembled into a total image. The magnetic resonance system has an image acquisition unit that acquires at least one first and at least one second image of the examination subject. Furthermore, an operating unit is provided with which the position of the at least one first and at least one second image are established in the examination subject and with which the measurement parameters are established for the first image and the second image. A number of images are advantageously acquired at the different positions of the examination subject. Furthermore, a control unit is provided that checks whether dependent measurement parameters are present under the established measurement parameters. The control unit adjusts the dependent measurement parameters such that they are identical for all images. The control unit in particular controls the measurement parameters such that, given a change of a dependent measurement parameter for one of the images, this change is transferred to the other images.

DESCRIPTION OF THE PREFERRED EMBODIMENTS

Figure 1:
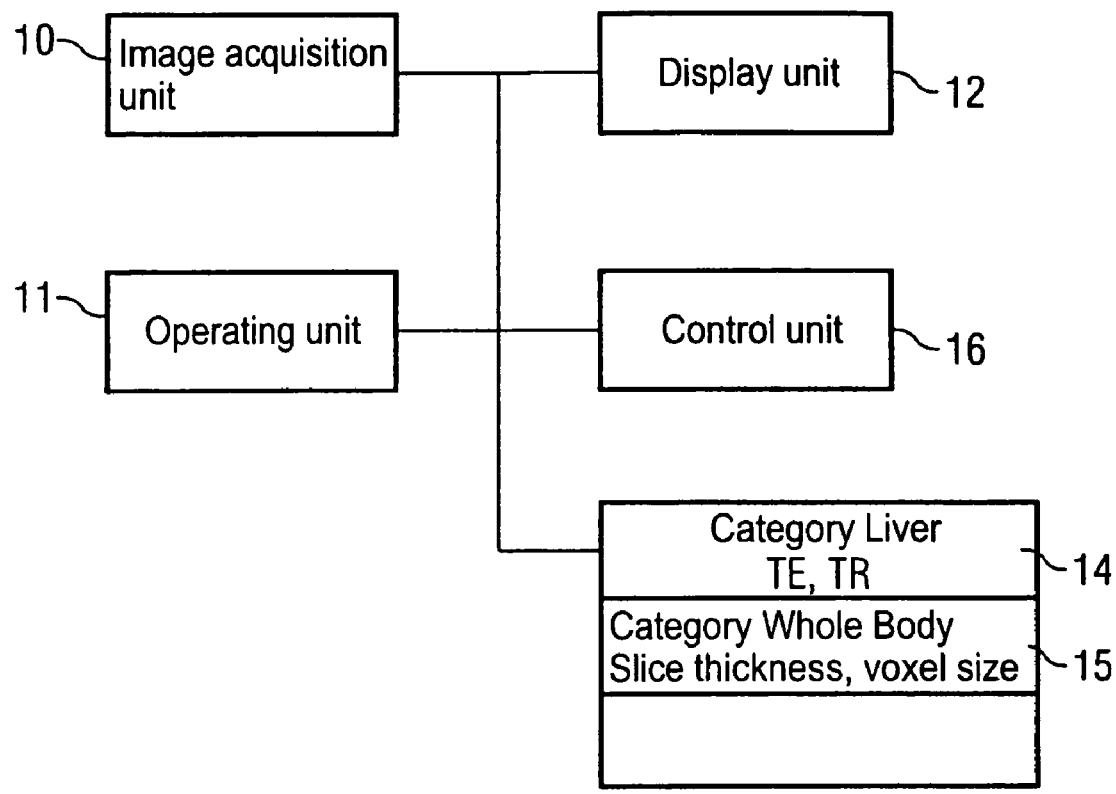
FIG. 1 schematically illustrates a magnetic resonance system according to the present invention.

Schematically shown in FIG. 1 is a magnetic resonance system with which the planning data acquisition in multiple regions of the examination subject is simplified. The mode of operation of a magnetic resonance system is known to those skilled in the art, such that only the components that are necessary for explanation of the invention are discussed.

Figure 2:
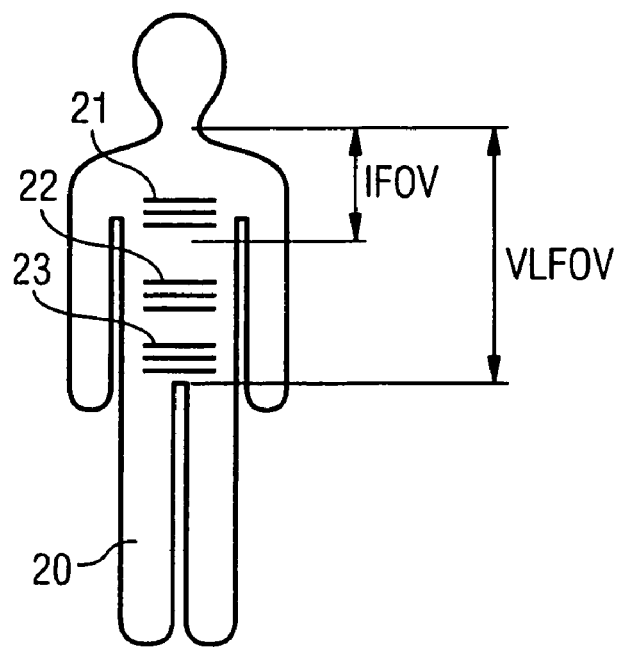
FIG. 2 schematically illustrates an examination person in whom images are acquired at different positions of the body.

The magnetic resonance system shown in FIG. 1 has an image acquisition unit 10 that can generate magnetic resonance images (MR images) of the examined person. An operating unit or control console 11 with whose help operating personnel can plan a complete measurement of the examination person, even given various table positions, is provided for planning of the measurement. For example, the positioning of the slices that should be used in the examination of the various body regions can ensue with the aid of the operating unit 11. An examination person 20 of whom exposures of the torso, for example, is to be made is schematically shown in FIG. 2. Some slice positions in which images of the examination person 20 are to be acquired are schematically represented with the reference characters 21, 22 and 23. The field of view or intrinsic field of view (IFOV) available in an examination is shown as well as the total region or the virtual large field of view (VLFOV) to be examined. This VLFOV can be examined only in the examination person 20 being moved through the magnet in steps, with a acquisition of a specific body region occurring at each table position.

Referring again to FIG. 1, the magnetic resonance system furthermore has a display unit 12 on which the images 10 acquired by the image acquisition unit 10 [sic] can be displayed, with which images 10 the operating personnel can detect, for example, the position of the slices that they place through the examination person 20 in the planning of the measurement. Furthermore, a storage unit 14 is provided that contains various data sets 15, each data set corresponding to a category. As shown in FIG. 1, each category can identify an anatomical region as well as comprise the measurement parameters that are dependent parameters in the acquisition, meaning that they should be the same for all acquired images at the different positions of the examination person in the magnet. For example, in the first data set of the liver (specified for illustration) the echo time TE and the repetition time TR are specified, which means that these measurement parameters should be the same in all measurements. A first measurement with a number of image sequences is typically acquired at a first table position, with the various imaging sequences and the associated measurement parameters for each table position being stored in a measurement protocol represented by a first measurement protocol data set.

A control unit 16 now ensures that the dependent parameters in the various measurements are identical in the different regions of the examination person. In the first data set 15 from FIG. 1, this means that the echo time and the repetition time are equally large for all measurements. In the further example specified in FIG. 1, given the selection of the category "whole body" it is ensured that, for example, the slice thickness, the voxel size are identical for all measurements. It can likewise be ensured that the imaging sequence used is identical, that the contrast is identical, or only a minimal variability of the contrast due to the changes of repetition time and echo time (and possibly the inversion time) exists.

The user can naturally configure new categories in which he or she selects the measurement parameters or, respectively, the symmetrical dependencies or the data post-processing steps between which a dependency should exist for an examination. The user can then assign a new name for this category and store this in the storage unit 14.

Figure 3:
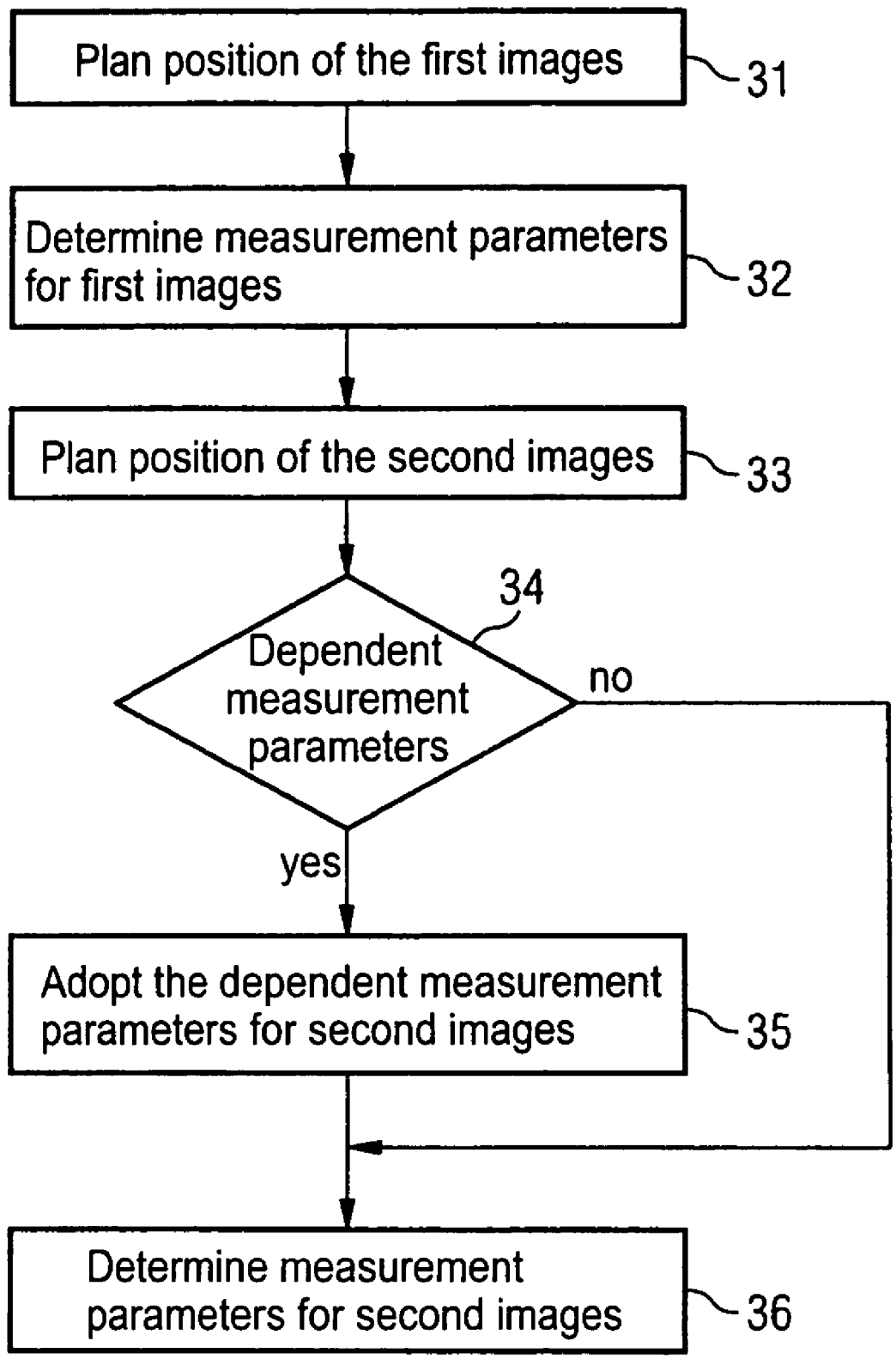
FIG. 3 is a flowchart for planning a measurement taking dependent measurement parameters into account.

A flowchart with the steps that help in the planning of an examination is exemplarily shown in FIG. 3. In a first step 31, for example, the position of the patient bed for the first images, or the position of the first images in the examination subject, is planned. The measurement parameters or the post-processing steps for the first images are likewise determined in a step 32. In a further step, further images must now be planned at a further position in the examination subject, whereby the position of the second images in the examination person is first planned in a step 33. In a next step 34 it is now checked whether dependent measurement parameters exist in the selected imaging sequence or, respectively, given the selection of the examination region. This can occur, for example, by the operating personnel determining the measurement parameters that should be dependent for the subsequent measurement via a display on the display unit 12 and selection of a category.

If dependent measurement parameters exist in the present measurement, the values of the measurement parameters that have been determined in the step 32 for the first images are automatically transferred to the second images, such that a manual adjustment by the operating personnel is no longer necessary (step 35). The remaining independent measurement parameters can be subsequently determined in a further step 36. These other individual measurement parameters do not depend on the selection of the measurement parameters for the first images. If the measurement protocols contain no dependent measurement parameters, the measurement parameters for the second images are thus likewise determined in the step 36 with the difference that all measurement parameters must now be individually set. For example, it is possible to show the dependent measurement parameters to the operating personnel in a manner that is optically different than that of the individual measurement parameters, such that the operating personnel immediately know that they are dependent measurement parameters.

Figure 4:
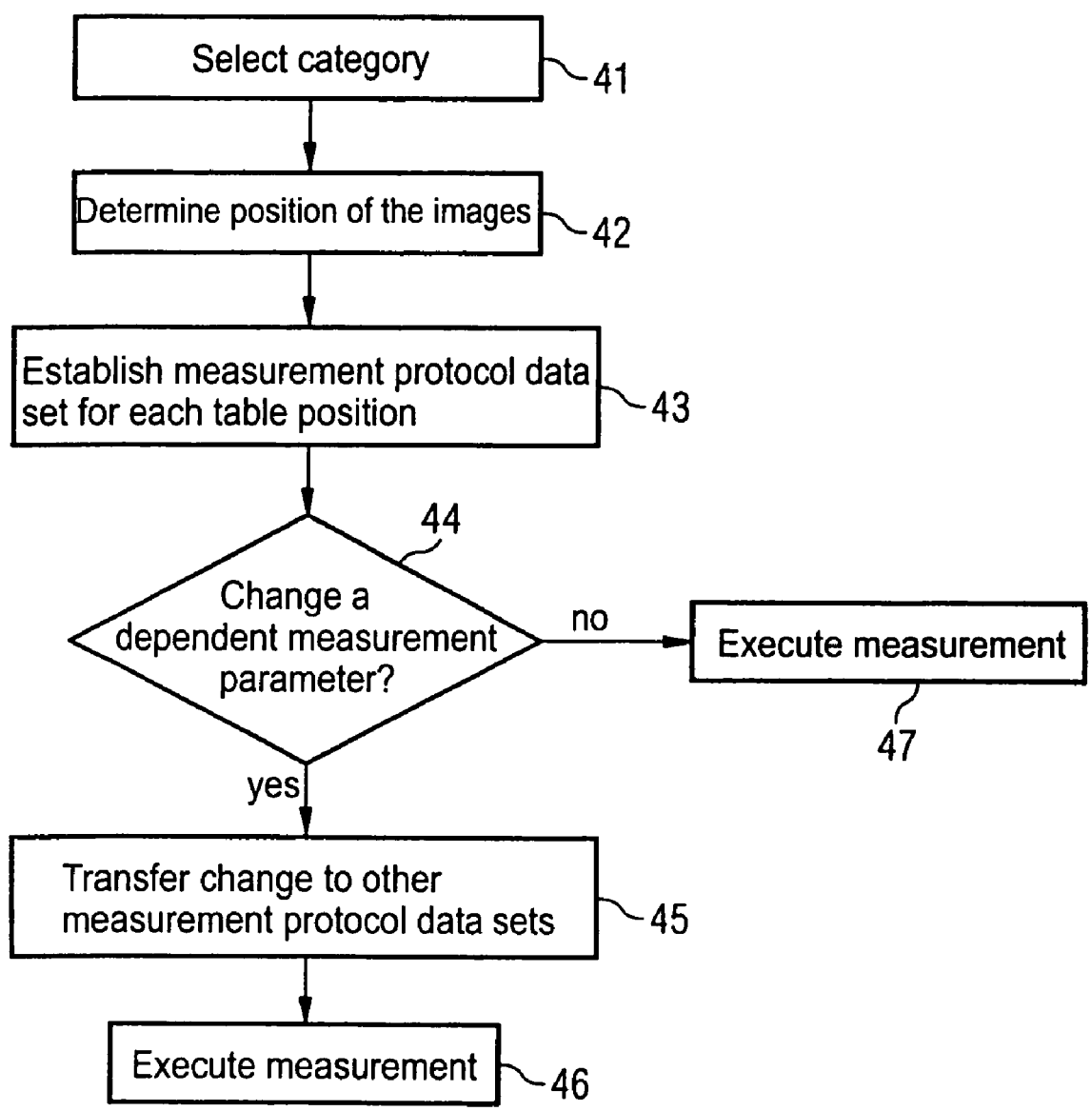
FIG. 4 is a flowchart for automatic transfer of changes of measurement parameters.

A further application of the invention is shown in FIG. 4. The operating personnel can select the category in a step 41, and the set of measurement parameters whose values are the same for all measurement protocols that participate in the examination is determined. The position of the individual images in the examination subject must subsequently be established in a step 42. The measurement protocol data set for each table position must likewise be established in a step 43, whereby this is possible in a simplified manner using the present invention since only the individual parameters must be set while the dependent measurement parameters must only be set for a measurement protocol. In a step 44 it is subsequently checked whether any dependent measurement parameters have possibly been changed. If this is the case, the change of this measurement parameter is transferred to other protocol data sets. When the changes have been transferred to all other measurement protocols, the measurement can subsequently be implemented in a step 46. If no dependent measurement parameter is changed in the step 44, the measurement can likewise be implemented in a step 47 after the measurement parameters and the position for the various images have been established.

As is apparent from the above embodiments, the present invention makes the planning of MR examinations easier since the time-intensive changing of measurement parameters in various examination regions is foregone. Each change of a dependent measurement parameter is automatically transferred to all further measurements of this examination.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for planning an examination of an examination subject in a magnetic resonance imaging system, comprising the steps of:
    determining a position of at least one first magnetic resonance image in an examination subject;
    establishing data acquisition parameters for acquiring data for said at least one first magnetic resonance image;
    determining a position of at least one second magnetic resonance image in the examination subject;
    establishing data acquisition parameters for acquiring data for said at least one second magnetic resonance image; and
    from among said data acquisition parameters for said at least one first magnetic resonance image and the data acquisition parameters for said at least one second magnetic resonance image, determining dependent data acquisition parameters, which can be set for both of said at least one first magnetic resonance image and said at least one second magnetic resonance image, and automatically identically setting said dependent data acquisition parameters in each of said data acquisition parameters for said at least one first magnetic resonance image and said data acquisition parameters for said at least one second magnetic resonance image.

2. A method as claimed in claim 1 comprising, upon a change of a dependent data acquisition parameter in one of said at least one first magnetic resonance image and said at least one second magnetic resonance image, transferring the changed dependent data acquisition parameter to the data acquisition parameters for the other of said at least one first magnetic resonance image and said at least one second magnetic resonance image, and upon a change of non-dependent data acquisition parameter in one of said at least one first magnetic resonance image and said at least one second magnetic resonance image, undertaking no transfer to the data acquisition parameters for the other of said at least one first magnetic resonance image and said at least one second magnetic resonance image.

3. A method as claimed in claim 1 comprising acquiring said data for said at least one first magnetic resonance image and said at least one second magnetic resonance image at different positions of a table on which the examination subject is disposed.

4. A method as claimed in claim 3 comprising generating a first data acquisition protocol, comprising a plurality of first protocol parameters in a first protocol data set, at a first of said different positions of said patient table, and generating a second data acquisition protocol, comprising a plurality of second protocol parameters in a second protocol data set, at a second of said table positions, and upon a change of a dependent parameter in one of said first or second protocol data sets, transferring the changed dependent parameter to the other of said first or second protocol data sets.

5. A method as claimed in claim 1 comprising generating categories of said dependent parameters, with each category comprising data acquisition parameters that are the same for all images.

6. A method as claimed in claim 5 comprising generating said categories dependent on respectively different examination regions of the examination subject.

7. A method as claimed in claim 1 comprising, at a display screen, displaying all of said data acquisition parameters for said at least one first magnetic resonance image and all of said data acquisition parameters for said at least one second magnetic resonance image and, at said display screen, displaying said dependent parameters differently from non-dependent data acquisition parameters.

8. A method as claimed in claim 7 comprising, by user interaction via said display screen, allowing manual selection of a category of said dependent parameters for a respective examination region of the examination subject, based on the dependent parameters at said display screen.

9. A magnetic resonance system comprising:
   a magnetic resonance data acquisition device that is adapted to interact with an examination subject to obtain data therefrom representing magnetic resonance images of the examination subject dependent on data acquisition parameters; and
   a computer programmed to determine that determines a position of at least one first magnetic resonance image in the examination subject, and to establish data acquisition parameters for said data acquisition device for acquiring data for said at least one first magnetic resonance image, and to determine a position of at least one second magnetic resonance image in the examination subject, and to establish data acquisition parameters for said data acquisition device for acquiring data for said at least one second magnetic resonance image, and from among said data acquisition parameters for said at least one first magnetic resonance image and the data acquisition parameters for said at least one second magnetic resonance image, and to determine dependent data acquisition parameters, which can be set for both of said at least one first magnetic resonance image and said at least one second magnetic resonance image, and to automatically identically set said dependent data acquisition parameters in each of said data acquisition parameters for said at least one first magnetic resonance image and said data acquisition parameters for said at least one second magnetic resonance image.

10. A magnetic resonance system as claimed in claim 9 comprising, wherein said computer programmed, upon a change of a dependent data acquisition parameter for one of said at least one first magnetic resonance image and said at least one second magnetic resonance image, to transfer the changed dependent data acquisition parameter to the data acquisition parameters for the other of said at least one first magnetic resonance image and said at least one second magnetic resonance image, and upon a change of a non-dependent data acquisition parameter in one of said at least one first magnetic resonance image and said at least one second magnetic resonance image, undertake no transfer to the data acquisition parameters of the other of said at least one first magnetic resonance image and said at least one second magnetic resonance image.

* * * * *